United States Patent
Liu et al.

(10) Patent No.: US 11,383,079 B2
(45) Date of Patent: Jul. 12, 2022

(54) ACTIVATION FIXATION LEAD FOR CARDIAC CONDUCTIVE SYSTEM PACING

(71) Applicant: Cardiac Pacemakers, Inc., St Paul, MN (US)

(72) Inventors: Lili Liu, St Paul, MN (US); Arthur J. Foster, Blaine, MN (US); Matthew J. Miller, Stillwater, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 47 days.

(21) Appl. No.: 16/722,470

(22) Filed: Dec. 20, 2019

(65) Prior Publication Data

US 2020/0197693 A1 Jun. 25, 2020

Related U.S. Application Data

(60) Provisional application No. 62/783,916, filed on Dec. 21, 2018.

(51) Int. Cl.
*A61N 1/05* (2006.01)
*A61N 1/362* (2006.01)

(52) U.S. Cl.
CPC .......... *A61N 1/0573* (2013.01); *A61N 1/362* (2013.01); *A61N 2001/058* (2013.01)

(58) Field of Classification Search
CPC ................ A61N 1/0573; A61N 1/362; A61N 2001/058
See application file for complete search history.

(56) References Cited

U.S. PATENT DOCUMENTS

| | | | | |
|---|---|---|---|---|
| 5,658,327 A * | 8/1997 | Altman | ................ | A61N 1/0573 607/127 |
| 8,160,721 B2 * | 4/2012 | Cooke | .................... | A61N 1/057 607/126 |
| 9,149,632 B1 * | 10/2015 | Vase | ..................... | A61N 1/0573 |
| 2003/0109914 A1 * | 6/2003 | Westlund | ............... | A61N 1/056 607/122 |
| 2005/0070988 A1 * | 3/2005 | Kawula | ................ | A61N 1/0575 607/126 |
| 2006/0036307 A1 * | 2/2006 | Zarembo | ................ | A61N 1/056 607/122 |
| 2008/0294229 A1 * | 11/2008 | Friedman | ............. | A61N 1/0573 607/127 |
| 2009/0259272 A1 * | 10/2009 | Reddy | .................. | A61N 1/0573 607/28 |
| 2010/0324636 A1 * | 12/2010 | Hill | ....................... | A61N 1/0573 607/116 |

* cited by examiner

*Primary Examiner* — Mallika D Fairchild
(74) *Attorney, Agent, or Firm* — Faegre Drinker Biddle & Reath LLP

(57) ABSTRACT

Various aspects of the present disclosure are directed toward apparatuses, systems, and methods that include an implantable lead. The lead may include a taper or tapered portion and a fixation helix both configured to embed within tissue. In addition, the apparatuses, systems, and methods may include a guide wire configured to obtain and record signals from the heart tissue and facilitate placement of the fixation helix.

7 Claims, 5 Drawing Sheets

ACTIVATION FIXATION LEAD FOR CARDIAC CONDUCTIVE SYSTEM PACING

CROSS REFERENCE TO RELATED APPLICATION

This application claims priority to Provisional Application No. 62/783,916, filed Dec. 21, 2018, which is herein incorporated by reference in its entirety.

TECHNICAL FIELD

The present disclosure relates to leads and stimulation systems. In particular, the present disclosure relates to leads and stimulation of the bundle of His or left or right bundle branch.

BACKGROUND

Cardiac rhythm management systems are useful for electrically stimulating a patient's heart to treat various cardiac arrhythmias. Placement of a lead for stimulation of the patient's heart may be difficult based on the location of a stimulation target, size of the stimulation target, and/or the depth of the stimulation target. The bundle of HIS, for example, is subsurface. The left and right bundle branches, for example, may be difficult to locate. There is a continuing need for improved targeting difficult stimulation targets such as the bundle of His and the left and right bundle branches.

SUMMARY

In Example 1, an implantable lead includes: an elongate body extending between a proximal end and a distal end and including at least one lumen extending between the proximal end and the distal end, the distal end of the elongate body configured to embed within heart tissue and reducing in diameter with a taper ending at the distal end and with a maximum diameter of the taper being substantially equal to a maximum outer diameter of the elongate body; and a fixation helix extending from distally from the at least one lumen and configured to rotate and therefore translate relative to the elongate body.

In Example 2, the implantable lead of Example 1, the lead is configured to embed at the heart tissue and the fixation helix is electrically active and configured to pace a left bundle branch or a right bundle branch of a patient.

In Example 3, the implantable lead of any one of Examples 1-2, the distal end of the lead body includes a tapered portion reducing the elongate body in diameter with the reduction in diameter having a minimum at the distal end.

In Example 4, the implantable lead of Example 3, wherein the tapered portion facilitates penetration into the heart tissue.

In Example 5, the implantable lead of any one of Examples 2-4, the tapered portion includes an outer diameter that is substantially equal to an outer diameter of the fixation helix.

In Example 6, the implantable lead of any one of Examples 1-5, the fixation helix is configured to extend beyond the distal end of the elongate body by between approximately 2 mm and approximately 4 mm.

In Example 7, the implantable lead of any one of Examples 1-6, the lead also includes a wire having a length to pass from the proximal end of the elongate body and extend outwardly from the distal end of the elongate body and configured to obtain and record signals from the heart tissue.

In Example 8, the implantable lead of Example 7, a distal end of the wire being configured to penetrate the heart tissue and facilitate placement of the fixation helix in the heart tissue.

In Example 9, the implantable lead of Example 8, the lead also includes an electrode arranged near the distal end of the elongate body, and wherein the fixation helix and the electrode are configured to pace the heart tissue and the wire is configured to simultaneously obtain and record signals from the heart tissue.

In Example 10, the implantable lead of Example 9, the electrode is arranged between approximately 3 mm and approximately 10 mm from the distal end of the elongate body.

In Example 11, the implantable lead of any one of Examples 7-10, the wire includes a proximal end, a distal end, and an insulated intermediate portion with the distal end of the wire being between approximately 2 mm and approximately 4 mm in length.

In Example 12, the implantable lead of Example 11, the proximal end of the wire is uninsulated and configured to interface with a mapping processor.

In Example 13, the implantable lead of any one of Examples 7-12, the wire includes markers arranged near a proximal end of the wire configured to control a penetration depth of the wire.

In Example 14, the implantable lead of Example 13, wherein a portion of the distal end of the wire is radiopaque.

In Example 15, the implantable lead of any one of Examples 1-14, at least a proximal portion of the fixation helix is insulated and at least one turn of a distal end of the fixation helix is uninsulated.

In Example 16, an implantable lead for pacing a left or right bundle branch of a patient's heart includes an elongate body extending between a proximal end and a distal end and including at least one lumen extending between the proximal end and the distal end, the distal end of the elongate body configured to embed within heart tissue and including a tapered portion reducing the elongate body in diameter with a minimum of the tapered portion at the distal end and a maximum diameter of the tapered portion being substantially equal to a maximum outer diameter of the elongate body; and a fixation helix extending from distally from the at least one lumen and configured to rotate and therefore translate relative to the elongate body.

In Example 17, the implantable lead of Example 16, the tapered portion facilitates penetration into the heart tissue.

In Example 18, the implantable lead of Example 16, the tapered portion includes an outer diameter that is substantially equal to an outer diameter of the fixation helix.

In Example 19, the implantable lead of Example 16, the fixation helix is configured to extend beyond the distal end of the elongate body by between approximately 2 mm and approximately 4 mm.

In Example 20, the implantable lead of Example 16, the lead also includes a wire having a length to pass from the proximal end of the elongate body and extend outwardly from the distal end of the elongate body and configured to obtain and record signals from the heart tissue.

In Example 21, the implantable lead of Example 20, a distal end of the wire being configured to penetrate the heart tissue and facilitate placement of the fixation helix in the heart tissue.

In Example 22, the implantable lead of Example 16, the lead also includes an electrode arranged near the distal end of the elongate body, and wherein the fixation helix and the electrode are configured to pace the heart tissue and the wire is configured as a unipolar electrode to simultaneously obtain and record signals from the heart tissue.

In Example 23, the implantable lead of Example 23, the fixation helix and the wire configured as bipolar electrodes to obtain and record signals from the heart tissue.

In Example 24, a system for pacing a patient's heart includes an implantable lead including: an elongate body extending between a proximal end and a distal end and including at least one lumen extending between the proximal end and the distal end, and a fixation helix extending from distally from the at least one lumen and configured to rotate and therefore translate relative to the elongate body; and a guide wire having a proximal end, a distal end, and an insulated intermediate portion and configured to obtain and record signals from the heart tissue and facilitate placement of the fixation helix.

In Example 25, the system of Example 24, the lead is configured to embed at the heart tissue and the fixation helix is electrically active and configured to pace a left bundle branch or a right bundle branch of the patient.

In Example 26, the system of Example 24, the fixation helix is electrically active and configured to pace a His bundle the patient.

In Example 27, the system of Example 24, the guide wire is configured as a unipolar electrode to obtain and record signals from the heart tissue.

In Example 28, the system of Example 24, the fixation helix and the guide wire are configured as bipolar unipolar electrodes to obtain and record signals from the heart tissue.

In Example 29, the system of Example 24, the distal end of the guide wire is between approximately 2 mm and approximately 4 mm in length and is configured to control a penetration depth of the guide wire.

In Example 30, the system of Example 27, the guide wire includes markers arranged near a proximal end of the wire configured to control a penetration depth of the wire.

In Example 31, a method of pacing a patient's heart includes delivering an implantable lead to a target location within a patient using a guide wire, the implantable lead including an elongate body extending between a proximal end and a distal end and including at least one lumen extending between the proximal end and the distal end, and a fixation helix extending from distally from the at least one lumen and configured to rotate and therefore translate relative to the elongate body; penetrating heart tissue at a His bundle or bundle branch with a distal end of the guide wire; obtaining signals from the heart tissue at the His bundle or the bundle branch with the guide wire; and penetrating the heart tissue with the fixation helix.

In Example 32, the method of Example 31, obtaining signals from the heart tissue with the guide wire includes operating the guide wire as a unipolar electrode.

In Example 33, the method of Example 31, obtaining signals from the heart tissue with the guide wire includes operating the guide wire and the fixation helix as bipolar electrodes.

In Example 34, the method of Example 31, penetrating the heart tissue with the fixation helix occurs while the guide wire is imbedded in the heart tissue.

In Example 35, the method of Example 31, penetrating heart tissue occurs at the bundle branch and the implantable lead includes a tapered portion reducing the elongate body in diameter with a minimum of the tapered portion at the distal end.

While multiple instances are disclosed, still other instances of the present invention will become apparent to those skilled in the art from the following detailed description, which shows and describes illustrative instances of the invention. Accordingly, the drawings and detailed description are to be regarded as illustrative in nature and not restrictive.

Figure 1:
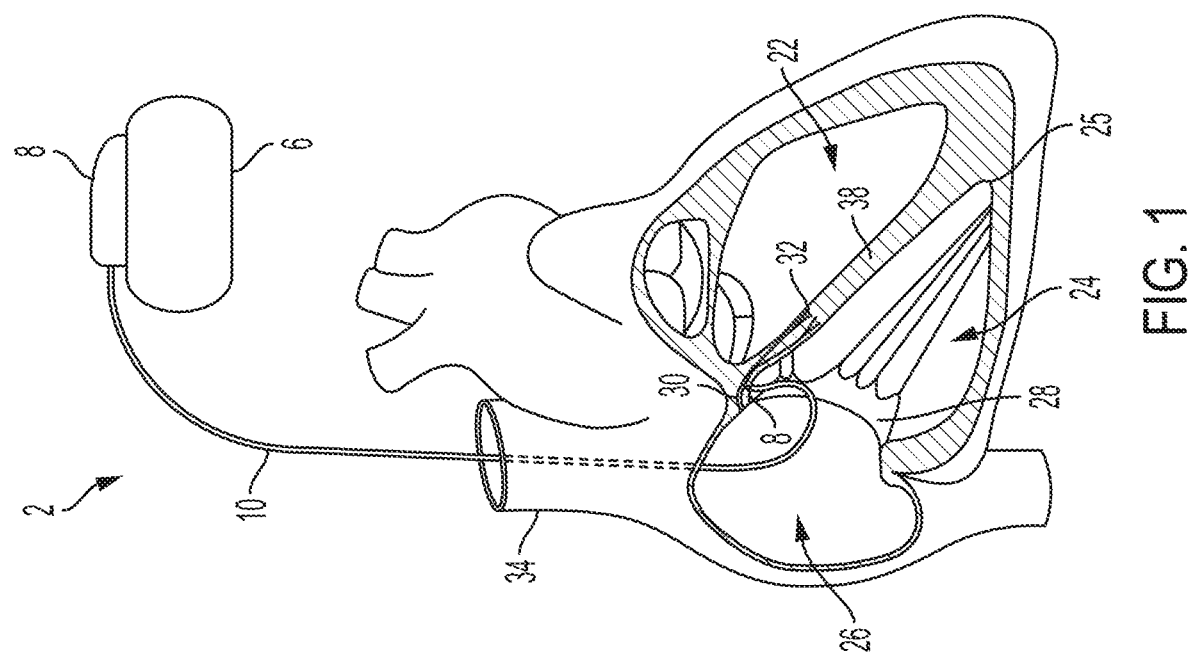
FIG. 1 a schematic diagram of a stimulation system including a pulse generator and a lead implanted in a patient's heart, in accordance with certain instances of the present disclosure.

While the invention is amenable to various modifications and alternative forms, specific instances have been shown by way of example in the drawings and are described in detail below. The intention, however, is not to limit the invention to the particular instances described. On the contrary, the invention is intended to cover all modifications, equivalents, and alternatives falling within the scope of the invention as defined by the appended claims.

DETAILED DESCRIPTION

Various aspects of the present disclosure are directed toward lead fixation and lead location. Certain leads, such as those discussed herein, may include a fixation helix that is embedded into tissue of the heart to fixate the lead, In certain instances, a lead tip or a distal end of the lead may shift or move while the lead or helix is rotated to fixate the lead. Various aspects of the present disclosure are directed toward a lead and guide wire that facilitates placement of the lead. The guide wire, for example, can be used to penetrate the heart tissue and map the targeted pacing location. The guide wire may penetrate the tissue in order to locate the targeted stimulation area along the heart tissue surface and also a penetration depth for the fixation helix. In addition, the guide wire may help stabilize and facilitate embedding of the fixation helix in the heart tissue.

Various aspects of the present disclosure are also directed toward a lead that may be embedded in the heart tissue. The left and right bundle branches, for example, are located within a septum of the heart. It may be beneficial for the fixation helix to be embedded in the septum in order to effectively pace the left bundle branch and/or right bundle branch. As compared to leads used in other areas of the heart that target areas of the heart having thin or fragile tissue, the lead itself may include a tapered distal end that embedded in the tissue wall when targeting the subsurface left bundle branch and/or right bundle for stimulation. In addition, the guide wire, as discussed above, may facilitate location of the left bundle branch and/or right bundle and penetration of the fixation helix.

The output of the heart is dependent on the synchrony of contraction within, and between, the chambers of the heart. Normally, each cardiac cycle is initiated by the depolarization of cells in the sinoatrial node which starts contraction of the cardiac muscle cells of the atria. The electrical impulse continues to the atrioventricular node, which delays propagation of the signal to allow the atria to contract before the ventricles. The distal portion of the atrioventricular node comprises the bundle of His. The bundle of His propagates the depolarization signal to left and right branches in the interventricular septum. The left and right branches propagate the depolarization signal to the left and right ventricles, respectively.

Various conditions can interfere with the normal electrical conduction system of the heart, which can result in arrhythmia and can compromise the output of the heart. For example, conduction block along the atrioventricular node can cause the atria and ventricles to contract out of rhythm. Conventional pacing therapies attempt to bypass the conduction system between the atria and ventricles by implanting a lead in the apex of the right ventricle where, ideally, each pulse delivered to cardiac muscle tissue propagates in a depolarization wave. However, direct stimulation of working myocardium (e.g., at the apex of the right ventricle) can result in slower propagation than direct stimulation of specialized conduction system fibers. For these and other reasons, it can be difficult to replicate the synchronous contractions of a natural conduction system by pacing at the apex of the right ventricle or other working myocardial site alone.

FIG. 1 illustrates a schematic diagram of a stimulation system 2 for direct stimulation of a patient's heart. In certain instances, the system 2 may be provided for direct stimulation of the bundle of His 30 or the left bundle branch and/or right bundle branch 32 within the septum 38 (between the left ventricle 22 and the right ventricle 24) as described in further detail. The stimulation system 2 includes an implantable pulse generator 6. The implantable pulse generator 6 can include circuitry for sensing bioelectrical signals and/or delivering electrical stimulation via one or more leads. The implantable pulse generator 6 can include a header 8 for connecting one or more leads to the implantable pulse generator 6. The header 8 can individually connect to respective contacts on the proximal end of the one or more leads, the contacts in respective electrical connection with electrical elements on the distal ends of the one or more leads (e.g., ring electrode, conductive helix) via conductors within the one or more leads.

As shown in FIG. 1, a lead 10 implanted is connected with the implantable pulse generator 6 through the header 8. The lead 10 operates to convey electrical signals between the bundle of His 30 or left/right bundle branches 32 and the implantable pulse generator 6. In various instances, the lead 10 enters the vascular system through a vascular entry site formed in the wall of the left subclavian vein, extends through the left brachiocephalic vein and the superior vena cava 34, traverses the right atrium 26, and is implanted in the right ventricle 24 proximate the bundle of His 30 or left/right bundle branches 32. In other instances, the lead 10 may enter the vascular system through the right subclavian vein, the left axillary vein, the left external jugular, the left internal jugular, or the left brachiocephalic vein, for example. Other suitable vascular access sites may be utilized in various other instances.

In certain instances, the lead 10 is a multi-polar medical electrical lead that includes a lead body formed from one or more materials, at least one lumen formed within the lead body, a proximal connector for interfacing with the implantable pulse generator 6, one or more electrical elements (e.g., ring electrodes, conductive helix) on the distal end of the lead 10, and one or more conductors for conducting electrical energy (e.g., bioelectrical signals, stimulation pulses) between the one or more electrical elements and the proximal connector. The lead 10 can have a flexible tubular body having an outer surface. The tubular body can be made from various materials such as silicone rubber and/or polymer material (e.g., polyurethane). In some cases, a distal portion of the lead is more flexible than a proximal portion of the lead. For example, the tubular body and external surface of the distal end of the lead 10, corresponding to a distal portion of the lead within the right ventricle 24 proximate the target simulation location, can be less stiff relative to a proximal portion that traverses the tricuspid valve 28 and continues to the lead interface 8. For example, the lead body and external surface of the distal portion can be made from silicone while the lead body and the external surface of the proximal portion can be made from polyurethane to configure the lead to have the distal portion be more flexible than the proximal portion.

The lead 10 can include a fixation element (e.g., a helix) 18 which can fix the lead 10 to cardiac tissue. The fixation element 18 can be electrically coupled to an electrical conductor (e.g., one or more coils or one or more cable conductors) extending to the proximal end of the lead 10 for interfacing with a channel of the implantable pulse generator 6. As such, a fixation element 18 can mechanically and electrically couple the lead 10 to the tissue and facilitate the transmission of electrical energy from the bundle of His 30 or left/right bundle branches 32 in a sensing mode and to the bundle of His 30 or left/right bundle branches 32 in a stimulation mode. As discussed in further detail below, the lead 10 may be used with a guide wire that can be configured to function as an electrode and penetrating structure to facilitate locating of a desired or effective stimulation location for the bundle of His 30 or left/right bundle branches 32. In instances where the lead 10 is used for pacing the left/right bundle branches 32, the lead 10 may include a portion that is embedded in the heart tissue.

Figure 2:
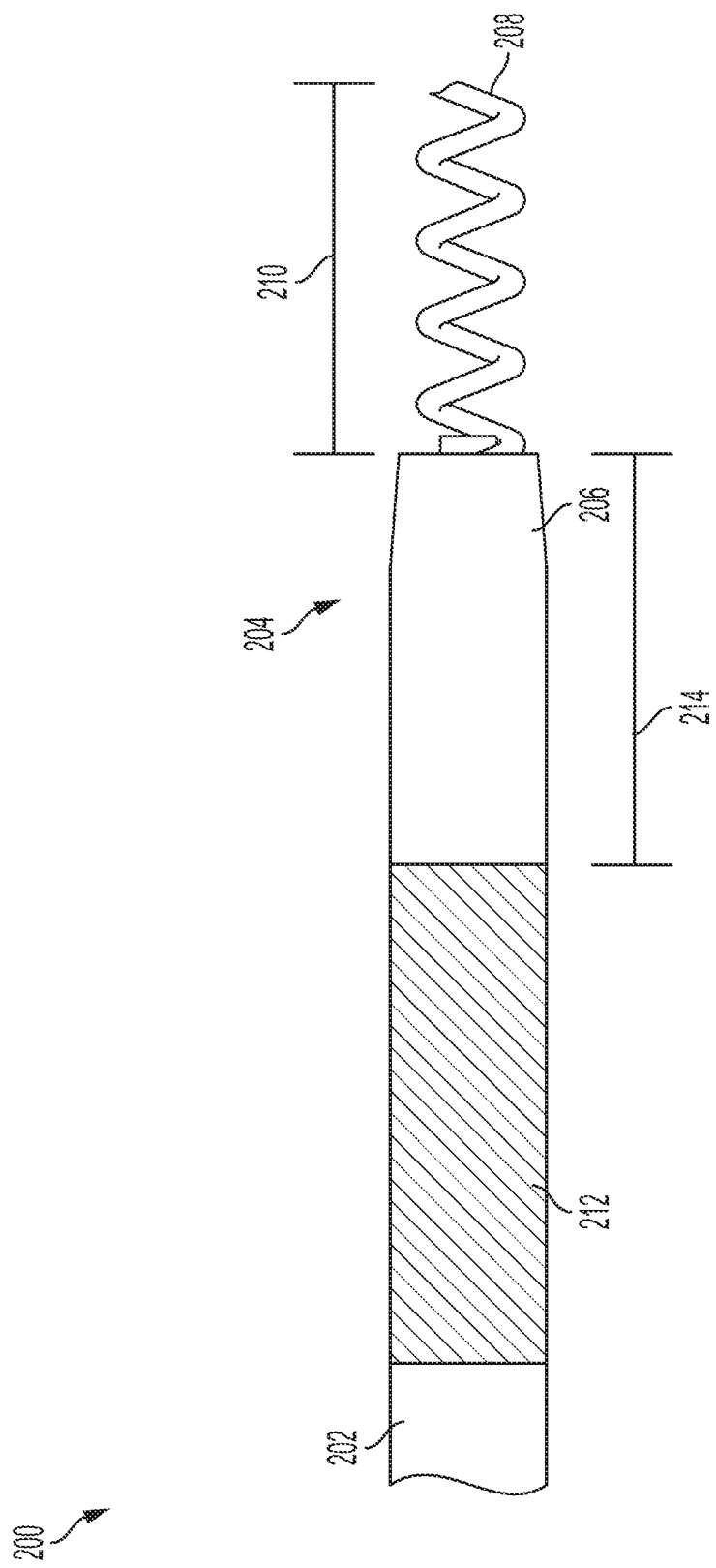
FIG. 2 is an illustration of an example implantable lead, in accordance with certain instances of the present disclosure.

FIG. 2 is an illustration of an example implantable lead 200, in accordance with certain instances of the present disclosure. The lead 200 shown in FIG. 2 is particularly used for stimulation of the left and/or right bundle branches. The lead 200, for example, includes an elongate body 202 that extends between a proximal end (not shown) that is configured to interface with an implantable pulse generator and a distal end 204.

Figure 3:
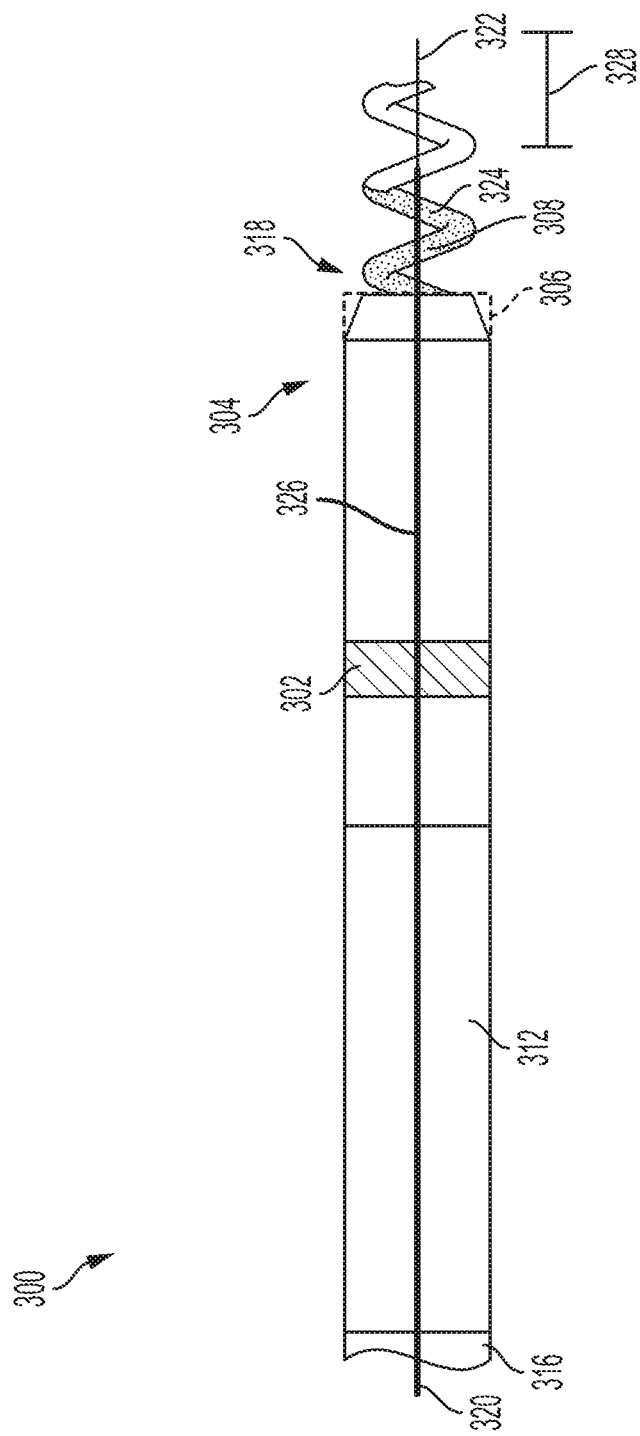
FIG. 3 is an illustration of an example implantable lead and wire, in accordance with certain instances of the present disclosure.

The elongate body 204 may also include a lumen (e.g., as shown in FIG. 3) that extends between the proximal end and the distal end 204. In addition and as shown, the distal end 204 may be configured to embed within heart tissue and reduce in diameter with a taper ending at the distal end 204. As shown in FIG. 2, the distal end 204 includes a tapered portion 206 that reduces the elongate body 204 in diameter. The tapered portion 206 facilitates embedding of the lead 200 into tissue. As shown, the tapered portion 206 includes a maximum diameter that is substantially equal to a maximum outer diameter of the elongate body 204.

In addition and as shown in FIG. 2, the elongate body 204 may also include a fixation helix 208 extending from distally from the at least one lumen of the elongate body 202 and configured to rotate and therefore translate relative to the elongate body 202. In certain instances, the fixation helix 208 may be configured to function as an electrode.

The tapered portion 206 max facilitate pacing for use with left bundle branch and/or right bundle branch stimulation (or other subsurface stimulation locations). As shown in FIG. 2, the tapered portion 206 reduces the elongate body 202 in diameter with the reduction in diameter having a minimum (or terminating) at the distal end 204. The lead 200 is to embed at the heart tissue and the fixation helix 208 is electrically active and configured to pace a left bundle branch or a right bundle branch of a patient. Leads configured to pace other portions of the heart may not include a taper or other similar structure that facilitates embedding of the lead within heart tissue due to tissue being thin or otherwise fragile. The left bundle branch and right bundle branch are within the heart septum, which is thicker or stronger than other portions of the heart. In addition, the left bundle branch and right bundle branch are subservice, therefore, it is beneficial for the fixation helix 208 to penetrate into the tissue deeper than other leads configured to penetrate other portions of the heart. The tapered portion 206 facilitates embedding (and penetration) of the fixation helix 208 to stimulate or pace the left bundle branch and/or right bundle branch.

As shown in FIG. 2, the tapered portion 206 may include an outer diameter that is substantially equal to an outer diameter of the fixation helix 208. In certain instances, the diameters being substantially equal may facilitate a transition between the fixation helix 208 and the tapered portion 206 and thereby facilitate embedding of the lead 200 within the heart tissue.

In certain instances, the fixation helix 208 is configured to extend beyond the distal end 204 of the elongate body 202 by between approximately 2 mm and approximately 4 mm (as compared to 1.8 mm, for example, in certain bradycardia leads). The length 210 of the fixation helix 208 may facilitate embedding of the electrically active embedding to target and stimulate the subsurface left or right bundle branches. In certain instances, the lead 200 may also include an electrode 212 arranged near the distal end 204 of the elongate body. The electrode 212 and the fixation helix 208 may be configured to stimulate the tissue in a bipolar manner. The electrode 212 may be spaced apart from the distal end 204 of the elongate body 202 by a length 214 where the length 214 is between approximately 3 mm and approximately 10 mm. In certain instances, the electrode 212 may be configured as anode and the fixation helix 208 may be configured as a cathode. In certain instances, the electrode 212 may be configured as cathode and the fixation helix 208 may be configured as a anode. The maximum diameter of the elongate body 206 includes the electrode 212. The maximum diameter of the elongate body 206 and the tapered portion 206 being substantially equal facilitates embedding (and penetration) of the tapered portion 206 into the tissue.

In certain instances, at least a proximal portion of the fixation helix 208 may be insulated and at least one turn of a distal end of the fixation helix 208 is uninsulated. One or more turns of the fixation helix 208 (e.g., internal to the lumen of the elongate body 202) may be covered by a dielectric or other insulative material as shown in FIG. 3. The proximal portion or turn of the fixation helix 208 being eliminated may minimize impedance interference that can result from the spacing of the electrode 212 and the fixation helix 208.

FIG. 3 is an illustration of an example implantable lead 300 and wire 320, in accordance with certain instances of the present disclosure. The lead 300 includes an elongate body 302 extending between a proximal end 316 and a distal end 304 and including a lumen 318. In certain instances, the lead 300 may include a tapered portion 306 reducing an outer diameter of the lead 300 in diameter with the taper ending at the distal end 304 (e.g., a minimum of the outer diameter of the elongate body 302 is at the distal end 304). As shown, the tapered portion 306 includes a maximum diameter that is substantially equal to a maximum outer diameter of the elongate body 302. In these instances, the lead 300 may be for pacing a left or right bundle branch of a patient's heart. In instances where the lead 300 does not include the tapered portion 306, the lead 300 may be configured to pace a bundle of HIS of the patient.

The tapered portion 306 may facilitate penetration of the lead 300 into the heart tissue. The lead 300 may also include a fixation helix 308 extending from distally from the at least one lumen 318 and configured to rotate and therefore translate relative to the elongate body 302. In certain instances, the tapered portion 306 may facilitate the fixation helix 308 more deeply penetrating the heart tissue of a patient's septum to pace the stimulate the left and/or right bundle branches.

Figure 4:
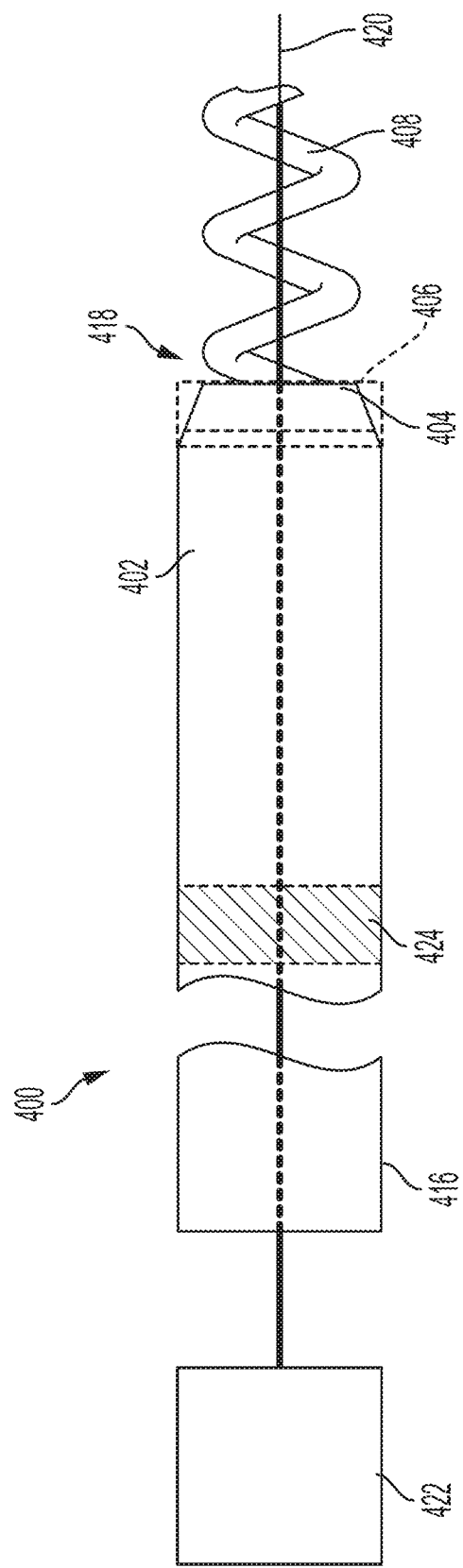
FIG. 4 is an illustration of another stimulation system including an implantable lead, in accordance with certain instances of the present disclosure.

As shown in FIG. 3, the lead 300 may cooperate and be usable with the wire 320. The wire 320 may have a length to pass from the proximal end 316 of the elongate body 302 and extend outwardly from the distal end 304 of the elongate body 304 and configured to obtain and record signals from the heart tissue. The wire 320 may function as a conductor when connected to a programmer or recording system (e.g., as shown in FIG. 4) to facilitate mapping or pacing of a target location. The wire 320 may allow a physician to measure electrical signals prior to embedding of the fixation helix 308 in the tissue. The wire 320 may also facilitate an amount of depth of penetration of the fixation helix 308 into the tissue as discussed in further detail below with reference to FIG. 4. In addition, a distal end 322 of the wire 320 may be configured penetrate the heart tissue and facilitate placement of the fixation helix in the heart tissue. In certain instances, the distal end 322 may be uninsulated, as compared to the remaining length 326 of the wire 320, to serve as an electrode. In certain instances, a length 328 of between approximately 0.5 cm and 3 cm of the distal end 322 of the wire 320 is uninsulated.

The lead 300 may also include an electrode 312 arranged near the distal end 304 of the elongate body 302. In certain instances, the fixation helix 308 and the electrode 312 are configured to pace the heart tissue and the wire 320 is configured as a unipolar electrode to simultaneously obtain and record signals from the heart tissue. Pacing with the electrode 312 and the fixation helix 308 may facilitate mapping with the wire 320 by showing real-time reaction of the heart to stimulation from the electrode 312 and the fixation helix 308. In other instances, the fixation helix 308 and the wire 320 are configured as bipolar electrodes to obtain and record signals from the heart tissue.

As shown in FIG. 3, the fixation helix 308 may include a proximal portion 324 that is insulated. The proximal portion 324 of the fixation helix 308 may be covered with an insulative material. In certain instances as noted above with reference to FIG. 2, the lead 300 may decrease impedance interference and maintain an appropriate pacing impedance between the fixation helix 308 and the electrode 312. In certain instances, the fixation helix 308 is extendable and retractable relative to the elongate body 302, and in other instances, the fixation helix 308 is fixed in relative to the elongate body 302. In instances where the fixation helix 308 is extendable and retractable, a terminal pin (not shown)

may be rotated to extend and retract the fixation helix 308 into tissue. In instances where the fixation helix 308 is fixed in relative to the elongate body 302, the elongate body 302 may be rotated to arrange the fixation helix 308 into tissue.

FIG. 4 is an illustration of another stimulation system including an implantable lead 400, in accordance with certain instances of the present disclosure. The system may also include a guide wire 420. The lead 400 includes an elongate body 402 extending between a proximal end 416 and a distal end 404 and including a lumen 418. The lead 400 may include an electrode 424 having a diameter substantially equal to an outer diameter of the elongate body 402. In certain instances, the lead 400 may include a tapered portion 406 reducing an outer diameter of the lead 300 in diameter with the taper ending at the distal end 404 (e.g., a minimum of the outer diameter of the elongate body 402 is at the distal end 404). The tapered portion 406 may have a maximum outer diameter that is substantially equal to an outer diameter of the lead body 402 (which includes the electrode 424). In these instances, the lead 400 may be for pacing a left or right bundle branch of a patient's heart. In instances where the lead 400 does not include the tapered portion 406, the lead 400 may be configured to pace a bundle of HIS of the patient.

The guide wire 420 may have a length to pass from the proximal end 416 of the elongate body 402 and extend outwardly from the distal end 404 of the elongate body 402 and configured to obtain and record signals from the heart tissue. The guide wire 420 may function as a conductor when connected to a programmer 422 or recording system to facilitate mapping or pacing of a target location. The guide wire 420 may allow a physician to measure electrical signals prior to embedding of the fixation helix 408 in the tissue. The programmer 422 may monitor the electrical signal and measure pacing impedance and confirm the stimulation site (e.g., His bundle or left and/or right bundle branches). In certain instances, the fixation helix 408 and an electrode (as shown in FIG. 3) on the elongate body 402 are configured to pace the heart tissue and the guide wire 420 is configured as a unipolar electrode to simultaneously obtain and record signals from the heart tissue. The programmer 422 may include circuitry configured to execute a mapping function. Based on detected electrical signals, the mapping signal programmer 422 outputs electrocardiograms (ECGs) to a display (not shown), which may be analyzed by the physician. The programmer 422 may facilitate depth of placement of the fixation helix 408 by showing a QRS wave morphology to a physician. The physician may alter a depth of penetration of the guide wire 420 to find the strongest signal for pacing by the fixation helix 408 and the lead 400.

In certain instances, pacing the patient's heart may include delivery the lead 400 to a target location (e.g., His bundle or left and/or right bundle branches) and penetrating heart tissue at a His bundle or bundle branch with the guide wire 420. Signals from the heart tissue are obtained at the His bundle or bundle branch with the guide wire 420 and the heart tissue may be penetrated with the fixation helix 408. Obtaining the signals from the heart tissue with the guide wire 420 may include operating the guide wire 420 as a unipolar electrode with bipolar pacing occurring between the electrode 454 and the fixation helix 408. In certain instances, obtaining signals from the heart tissue with the guide wire 420 includes operating the guide wire 420 and the fixation helix 408 as bipolar electrodes. A proximal end (e.g., shown in FIG. 5) of the guide wire 420 may be coupled to the programmer 422 during lead 400 placement.

In certain instances, selection between conductor structures (e.g., electrode 424 and helix 408) can facilitate accurate and localized pacing. For example and as discussed in detail, the tapered portion 406 may be embedded into tissue when pacing a patient's left bundle branch or right bundle branch. The left bundle branch is further embedded, relative to the positioning of the lead 400 as shown in FIG. 1, than the right bundle branch. In certain instances, the depth of pacing may be altered by changing which of the electrode 424 and helix 408 is selected as the cathode and which of the electrode 424 and helix 408 is selected as the anode. In certain instances, the helix 408 may be selected as the cathode when pacing the left bundle branch and the electrode 424 may be selected as the cathode when pacing the right bundle branch. The tapered portion 406 may facilitate arrangement of the electrode 424 near the target left bundle branch or right bundle branch by embedding a portion of the lead 400 into tissue and brining the electrode 424 closer to the target pacing location than if the lead 400 was not embedded. The helix 408 being partially insulated, as noted above, maintains the appropriate pacing impendence. he pacing depth may be determined or verified with the guide wire 420 as note above.

Figure 5:
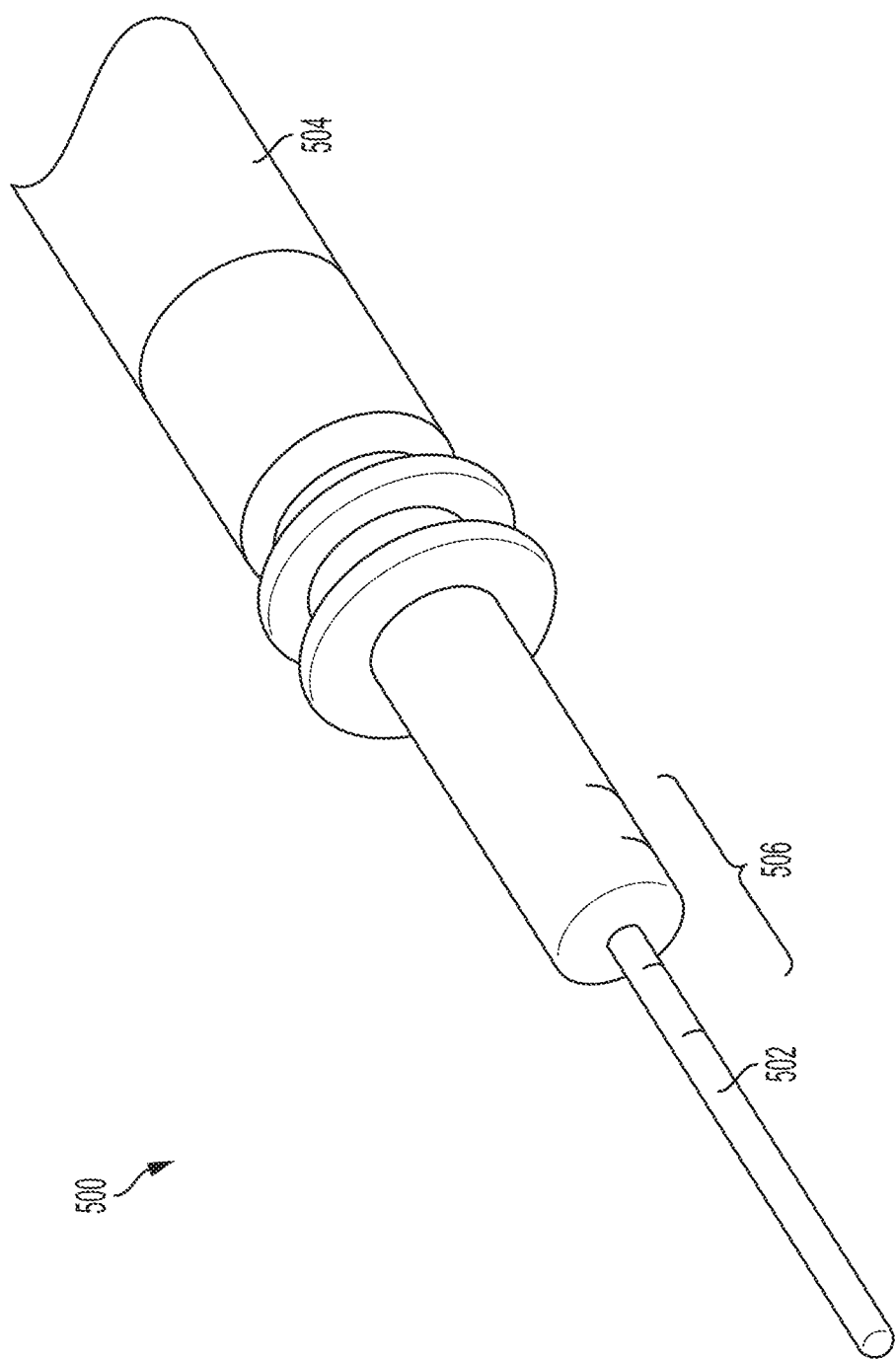
FIG. 5 is an illustration of an example wire, in accordance with certain instances of the present disclosure.

FIG. 5 is an illustration of an example wire 500, in accordance with certain instances of the present disclosure. As detailed above, the guide wire 500 may facilitate an amount of depth of penetration of a fixation helix or lead into the tissue as discussed in further detail below with reference to FIG. 4. In addition, a distal end 502 of the guide wire 500 may be configured to penetrate the heart tissue and facilitate placement of the fixation helix in the heart tissue. In certain instances, the distal end (as shown in FIG. 3) may be uninsulated, as compared to a remaining length of the wire 500, to serve as an electrode.

As shown in FIG. 5, the guide wire 500 includes an insulated intermediate portion 504. In addition, the proximal end 502 may not be insulated to enable connection to a controller. In certain instances, the proximal end 502 of the guide wire 500 may include a series of markers 506. The markers 506 may be arranged near the proximal end 502 of the guide wire 500 to control a penetration depth of the wire 500.

The markers 506 may be a visual indicator to an operating physician as to a depth of penetration of the distal end of the guide wire 500. The guide wire 500 may be removably arranged through a lead body (not shown) and used as a guide wire 500 for arranging the lead body at a target location. The amount of length of the guide wire 500 arranged within the lead body may correspond to an amount of extension of the guide wire 500 from the distal end of the lead body. The markers 506 on the proximal end 502 of the guide wire 500 may correspond to an amount of extension of the guide wire 500 beyond the distal end or beyond a fixation helix and show the operating physician ad depth of guide wire 500 penetration.

Various modifications and additions can be made to the exemplary instances discussed without departing from the scope of the present invention. For example, while the instances described above refer to particular features, the scope of this invention also includes instances having different combinations of features and instances that do not include all of the described features. Accordingly, the scope of the present invention is intended to embrace all such alternatives, modifications, and variations as fall within the scope of the claims, together with all equivalents thereof.

We claim:

1. An implantable lead for pacing a left or right bundle branch of a patient's heart, the implantable lead comprising:
an elongate body extending between a proximal end and a distal end and including at least one lumen extending between the proximal end and the distal end, the distal end of the elongate body configured to embed within heart tissue and including a tapered portion reducing the elongate body in diameter with a minimum diameter of the tapered portion at the distal end and a maximum diameter of the tapered portion being equal to a maximum outer diameter of the elongate body;
a fixation helix having an outer diameter and the fixation helix extending from distally from the at least one lumen and configured to rotate and therefore translate relative to the elongate body;
wherein the minimum diameter of the tapered portion is equal to the outer diameter of the fixation helix; and
an electrode structure located proximally of and spaced from the tapered portion of the elongate body by a distance of between 3 mm and 10 mm.

2. The implantable lead of claim 1, wherein the tapered portion facilitates penetration into the heart tissue.

3. The implantable lead of claim 1, wherein the fixation helix is configured to extend beyond the distal end of the elongate body by between 2 mm and 4 mm.

4. The implantable lead of claim 1, further comprising a wire having a length to pass from the proximal end of the elongate body and extend outwardly from the distal end of the elongate body and configured to obtain and record signals from the heart tissue.

5. The implantable lead of claim 4, wherein a distal end of the wire being configured to penetrate the heart tissue and facilitate placement of the fixation helix in the heart tissue.

6. The implantable lead of claim 4, further comprising the electrode structure arranged near the distal end of the elongate body, and wherein the fixation helix and the electrode are configured to pace the heart tissue and the wire is configured as a unipolar electrode to simultaneously obtain and record signals from the heart tissue.

7. The implantable lead of claim 6, wherein the fixation helix and the wire configured as bipolar electrodes to obtain and record signals from the heart tissue.

* * * * *